(12) United States Patent
Parekh et al.

(10) Patent No.: US 12,220,322 B2
(45) Date of Patent: Feb. 11, 2025

(54) PROCESS, KIT, AND IMPLANT FOR CORRECTION OF A BONE INJURY

(71) Applicant: Paragon Advanced Technologies, Inc., Englewood, CO (US)

(72) Inventors: Selene G. Parekh, Durham, NC (US); Luciano Bernardino Bertolotti, Denver, CO (US); Gregory J. Kowalczyk, Little Silver, NJ (US)

(73) Assignee: Paragon Advanced Technologies, Inc., Englewood, CO (US)

( * ) Notice: Subject to any disclaimer, the term of this patent is extended or adjusted under 35 U.S.C. 154(b) by 0 days.

(21) Appl. No.: 18/165,534

(22) Filed: Feb. 7, 2023

(65) Prior Publication Data

US 2023/0255784 A1 Aug. 17, 2023

Related U.S. Application Data

(63) Continuation of application No. 16/537,335, filed on Aug. 9, 2019, now Pat. No. 11,571,312.

(60) Provisional application No. 62/717,862, filed on Aug. 12, 2018.

(51) Int. Cl.
| | |
|---|---|
| *A61B 17/17* | (2006.01) |
| *A61F 2/42* | (2006.01) |
| *A61F 2/46* | (2006.01) |
| *A61B 17/56* | (2006.01) |
| *A61F 2/30* | (2006.01) |

(52) U.S. Cl.
CPC ........ *A61F 2/4225* (2013.01); *A61B 17/1775* (2016.11); *A61F 2/4606* (2013.01); *A61B 2017/565* (2013.01); *A61F 2002/30622* (2013.01)

(58) Field of Classification Search
CPC .................. A61F 2/4225; A61F 2/4606; A61F 2002/30622; A61B 17/1775; A61B 17/151; A61B 17/1739; A61B 17/8004; A61B 17/8014; A61B 17/8052; A61B 17/8057; A61B 17/8061; A61B 2017/565
See application file for complete search history.

(56) References Cited

U.S. PATENT DOCUMENTS

| | | | | |
|---|---|---|---|---|
| 5,087,260 | A * | 2/1992 | Fixel | A61B 17/746 606/65 |
| 7,316,687 | B2 * | 1/2008 | Aikins | A61B 17/1668 606/86 A |
| 8,523,919 | B2 | 9/2013 | Huebner | |
| 9,060,822 | B2 * | 6/2015 | Lewis | A61B 17/8605 |
| 9,681,904 | B2 * | 6/2017 | Wolf | A61B 17/1728 |
| 11,571,312 | B1 * | 2/2023 | Parekh | A61B 17/1728 |

(Continued)

*Primary Examiner* — Tracy L Kamikawa
(74) *Attorney, Agent, or Firm* — Heslin Rothenberg Farley & Mesiti P.C.

(57) ABSTRACT

There is a process for correcting a bone injury, an implant for correcting the bone injury and a kit for applying the implant for correcting the bone injury. The process can be made substantially uniform with the application of a standardized kit. In at least one application the process is for correcting a bunion on a patient. The process can include applying a first drill guide to a bone, and then a second drill guide. Once the drill guides have been applied and wires have been inserted into a bone, an implant can then be applied to correct a bone injury and to allow the bone injury to heal.

14 Claims, 10 Drawing Sheets

(56) References Cited

U.S. PATENT DOCUMENTS

| | | | |
|---|---|---|---|
| 2009/0036931 A1* | 2/2009 | Pech | A61B 17/7291 |
| | | | 606/62 |
| 2014/0148859 A1* | 5/2014 | Taylor | A61B 17/8615 |
| | | | 606/282 |
| 2014/0180348 A1 | 6/2014 | Thoren | |
| 2016/0270800 A1* | 9/2016 | Sanders | A61B 17/17 |
| 2017/0164989 A1* | 6/2017 | Weiner | A61B 17/8061 |

\* cited by examiner

PROCESS, KIT, AND IMPLANT FOR CORRECTION OF A BONE INJURY

CROSS-REFERENCE TO RELATED APPLICATION

This application is a continuation of U.S. patent application Ser. No. 16/537,335, filed Aug. 9, 2019 and entitled Process, Kit, and Implant for Correction of a Bone Injury, which issued as U.S. Pat. No. 11,571,312 on Feb. 7, 2023, which claims priority benefit under 35 U.S.C. § 119 (e) of U.S. Provisional Patent Application No. 62/717,862, filed Aug. 12, 2018, and entitled Process, Kit, and Implant for Correction of a Bone Injury, which are incorporated herein by reference in their entireties

BACKGROUND OF THE INVENTION

At least one embodiment of the invention relates to a bunion correction system which is configured to correct a bunion by realigning a metatarsal section of a foot. Many times, with bunions, there is a rotational deformity with a metatarsal wherein the angle should be closer to 10 degrees. With a bad bunion the angle of rotation could be closer to 20 degrees. Therefore, there is a need for an implant and a treatment process for treating a bunion on a foot.

SUMMARY OF THE INVENTION

As indicated above, there is a need to fix a bunion with a pre-designed treatment process. This process can include both an implant and a kit for applying an implant as well. With respect to the process, a patient's foot or body part is scanned. Next, a scan is sent to a doctor wherein the patient's bone structure is reviewed based upon an internal scan. With bunions, there is a deformity of the metatarsal. With a healthy individual, the normal angle between the 1st and 2nd toes (IM angle) should be closer to 10 degrees. In severe bunions it could be over 20 degrees. In addition, with bunions, there is a rotational deformity. The sesamoids (under the head of the metatarsal) is not directly under the bone where it belongs. Thus, treatment requires that a professional determine what angle cut to make on the bone, and how much is needed to rotate the sesamoids, to bring them directly plantar under the metatarsal head and to bring the angle back to 10 degrees.

Once a professional can determine this, a CAD can be used to design cutting guides that marry with a plate to guide a surgeon to make the exact correction pre-planned in the analysis. The guides and the plate are 3D printed.

For example, guides are placed on the bone (they only fit in one place since they match perfectly the profile of the metatarsal. These guides are held in place with wires that are inserted into the bone. The wire holes are in a specific location to match with the plate to make the required correction. In addition, the guides also have a slot to ensure the angle of cut is accurate. The guides do not have a slot to cut, but small holes to make provisional marks in the bone to cut later.

Next, the guides are two pieces so that it can be removed once the kwires are in place for example, the kwires are not in the same plane.

Another guide is placed to guide the surgeon where to remove a small piece of bone (recess) to allow for the bottom of the plate fit on the bone). One the plate, is set, the matching screw hole is recessed to avoid soft tissue irritation.

Next, the surgeon removes the guides and makes the osteotomy but leaves the kwires in place.

Next, the surgeon places the implant on the bone. The implant is in the form of a plate however, it has holes in it to accept the wires. But to make the plate fit against the bone, he must rotate the head of the metatarsal until the wires can enter the plate holes. Again, all of this is preplanned, using a kit thus, the surgeon can predetermine how much this will rotate the sesamoids and re-angle the bone. Finally, an underlying implant plate is secured with screws.

The process can use an implant for fusing bone together. The implant can comprise at least one plate having a first end section, a second end section and a middle section. There are a plurality of holes comprising a set of wire holes, and a set of screw holes wherein the wire holes are configured to receive wires used to place the implant on a bone, and wherein the screw holes are configured to receive screws to secure the implant to a bone.

The implant can be part of a kit for setting an implant comprising a first drill guide used to set wires in a bone, and a second drill guide used to remove a portion of the bone.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

To correct a bunion there is proposed a kit comprising at least one drill guide such as drill guide 100 (See FIG. 1A), a second drill guide (See FIG. 2C) and an implant (See FIGS. 5A-7D). Once the drill guides such as drill guide 100 and drill guide 120 establish sufficient drill holes in a bone such as a metatarsal bone, the implant can be inserted and fixed to a bone to fuse the bone together.

Figure 1A:
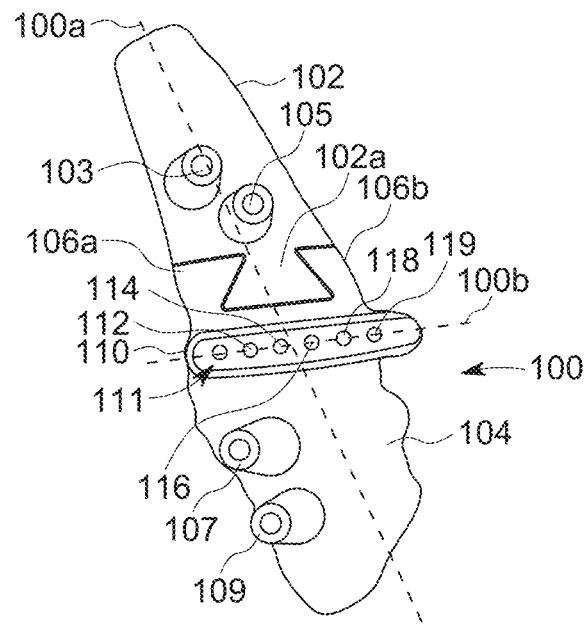
FIG. 1A is a top view of a first drill guide for use with an implant for use on a toe.

For example, FIG. 1A shows a top view of a first drill guide 100. The first drill guide has a longitudinal line 100a. Longitudinal line 100a extends along the length of the drill guide 100. Drill guide 100 comprises a plurality of parts, including a first plate section 102, and an insert of the first plate section 102A. Disposed in first plate section 102 is a screw hole 103, another screw hole 105. A second plate section 104 also includes a first screw hole 107, and a second screw hole 109. There is also a central ridge 110, which extends along a bisecting latitudinal line 100B. Central ridge 110 includes plurality of wire holes including wire hole 111, wire hole 112, wire hole 114, tadpole 116, wire hole 118, and wire hole 119.

Figure 1B:
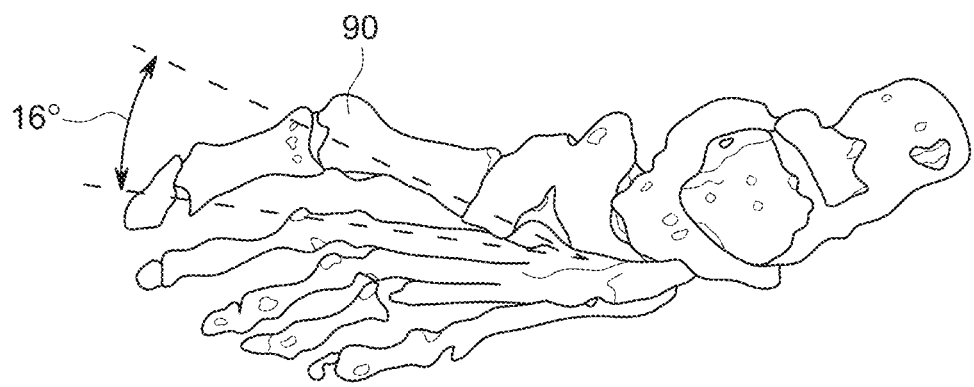
FIG. 1B is a top view of a foot which may need repair.
Figure 1C:
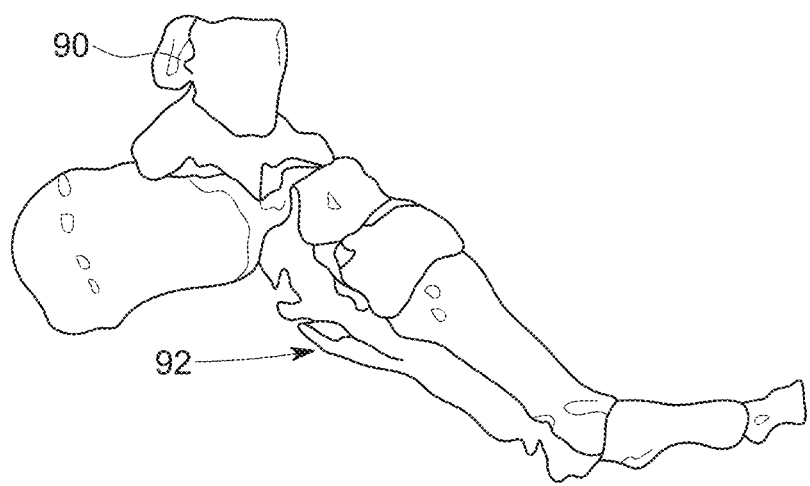
FIG. 1C is a side view of a foot.
Figure 2A:
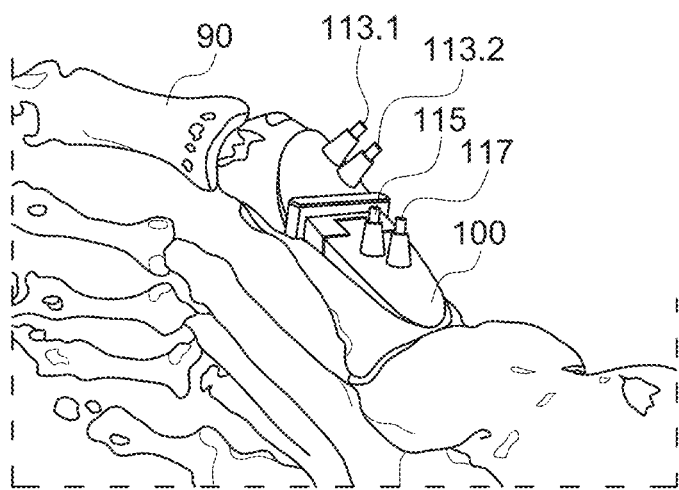
FIG. 2A is a side view of a foot with a first drill guide.

FIG. 1B shows a top view of a foot 90. Foot 90 includes a first main toe which is offset from another toe by approximately 16°. This condition shows the need for a correction of a bunion. FIG. 1C shows the side view of a foot 90 having an arch section 92. FIG. 2C shows a side view of a foot which has an instep section 94, and a base implant 120, coupled to a toe. Base implant 120 is shown in greater detail in FIG. 4C.

Figure 2B:
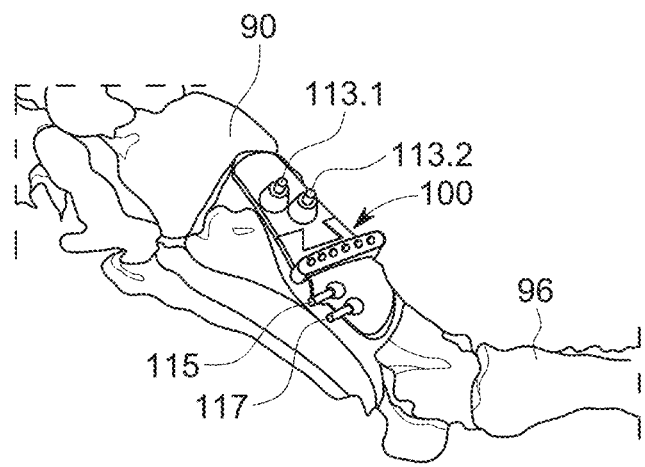
FIG. 2B is a side view of a foot with the drill guide of FIG. 1A.
Figure 2C:
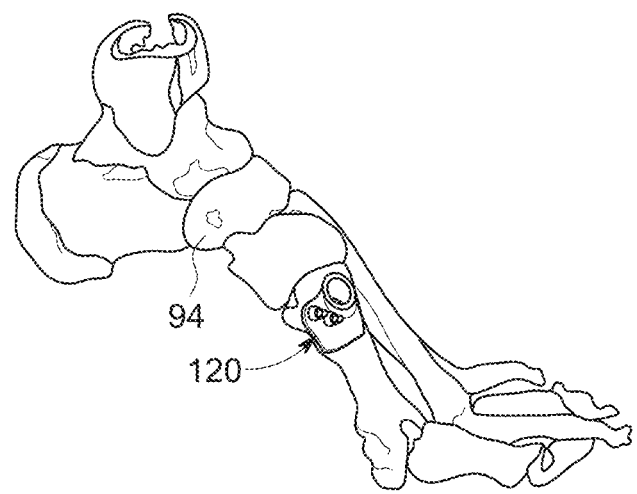
FIG. 2C is a view of a foot with a second drill guide.

FIG. 2B shows a side view of the drill guide 100 coupled to a toe 96. This side view of drill guide 100 also includes a plurality of wires 113.1, 113.2, 115, and 117.

Figure 3A:
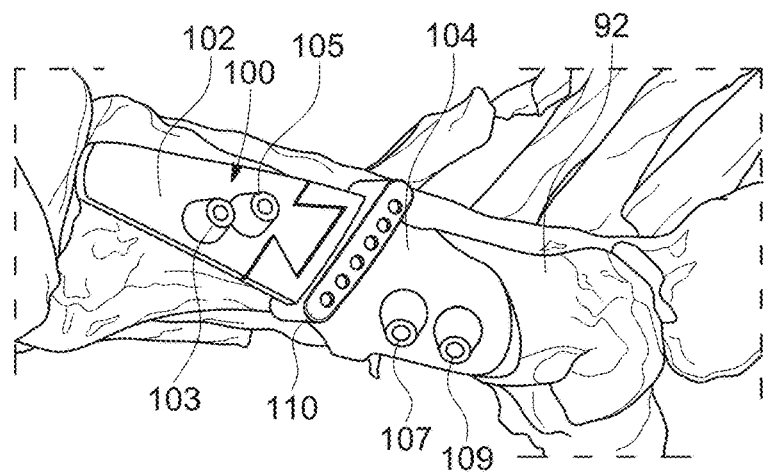
FIG. 3A is a side view of a toe with the drill guide inserted therein.
Figure 3B:
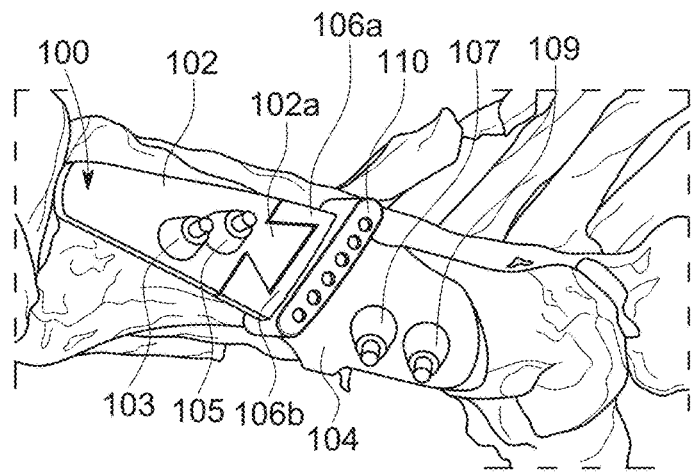
FIG. 3B is another side view of the drill guide as well.
Figure 3C:
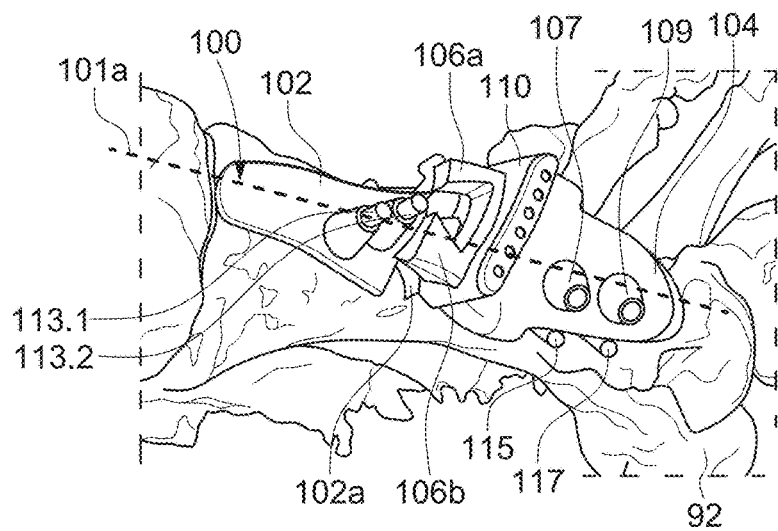
FIG. 3C is another side view of the drill guide.

FIG. 2A shows a side view of toe which has plate 100 coupled to it. In addition, there is shown wires 113.1, 113.2, 115, and 117 extending out from plate 100. These wires are configured to secure plate 100 to an adjacent bone. FIG. 3A shows a view of plate 100 coupled to an adjacent metatarsal bone. FIG. 3B shows a view of plate 100 with the first plate section 102, and insert 102A, positioned adjacent to wings 106 a and 106B. There is also raised wire holes 103 and 105 extending out transverse to a front surface of plate 100 and a region of first plate section 102. These raised wire holes are formed as substantially conical raised wire holes. The insert 102 a is configured to form a tongue and groove connection with wings 106A and 106B. A central ridge 110 extends substantially transverse to longitudinal extension of plate 100. Central ridge 110 includes a plurality of wire holes extending along the extension of ridge 110. Second plate section 104 includes a plurality of raised wire holes 107 and 109. FIG. 3C shows plate 100 having longitudinal axis 101a. This view shows first plate section 102 being separate from second plate section 104. In addition, wings 106A and 106B are shown as separate from insert 102A. In this view, second plate section 104 is shown being placed over wires 115, and 117 which extend out from metatarsal bone 92. In this view, second plate section 104 can then be removed from wires 115 and 117 via wire holes 107 and 109.

Figure 4A:
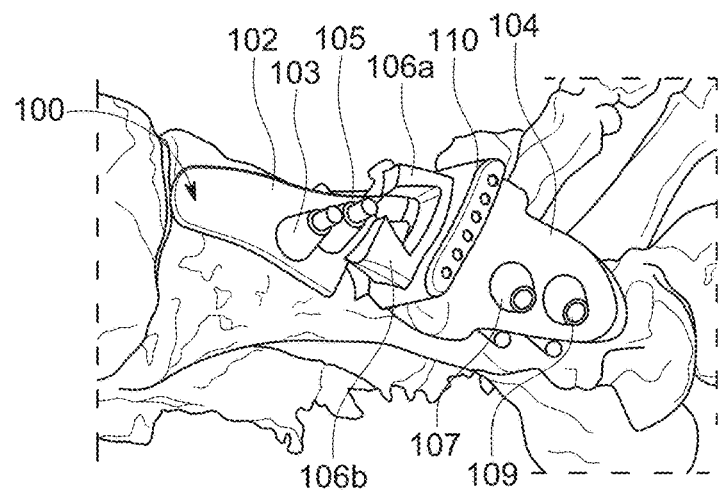
FIG. 4A is a side view of the drill guide with a portion of the piece removed.
Figure 4B:
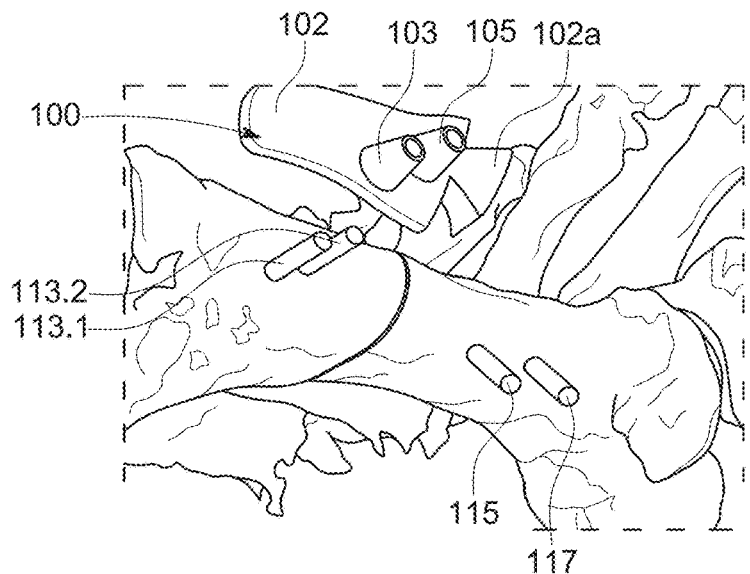
FIG. 4B is a view of the drill guide that is being removed from the bone.
Figure 4C:
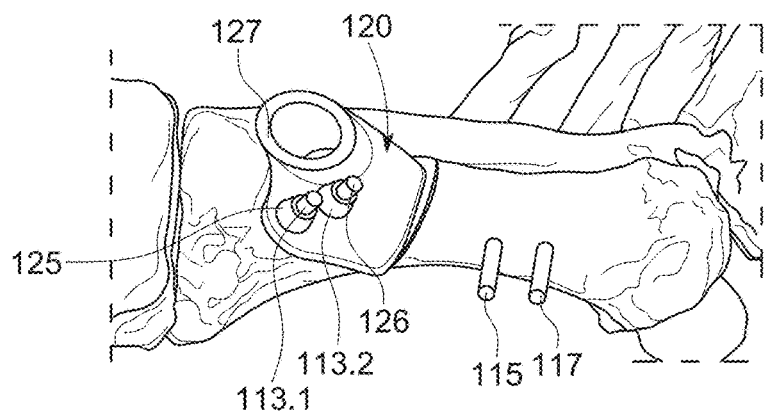
FIG. 4C is another view of a second drill guide being inserted after the first drill guide.

FIG. 4A shows another view of this second plate section 104 being removed from the metatarsal bone 92. Once this second plate section 104 is removed the first plate section 201 102 can be removed wherein plate 102 is slid off from wires 113.1 and 113.2 via wire holes 103 and 105. This leaves metatarsal bone 92 exposed with wires 113.1 and 113.2 as well as wires 115 and 117 exposed. Next, in FIG. 4C there is shown a second drill guide 120 being inserted onto wires 113.1 and 113.2. Drill guide 120 has a screw hole 127. Drill guide 120 is inserted onto wires 113.1 and 113.2 via wire holes 125 and 126. Drill guide 120 allows drill holes to be inserted therein such as through screw hole 127. Screw hole 127 extends substantially transverse to an extension of wire holes 125 and 126 allowing for a transverse extension of a screw which is transverse to an extension of wires 113.1 and 113.2 extending through wire holes 125 and 126.

Figure 5A:
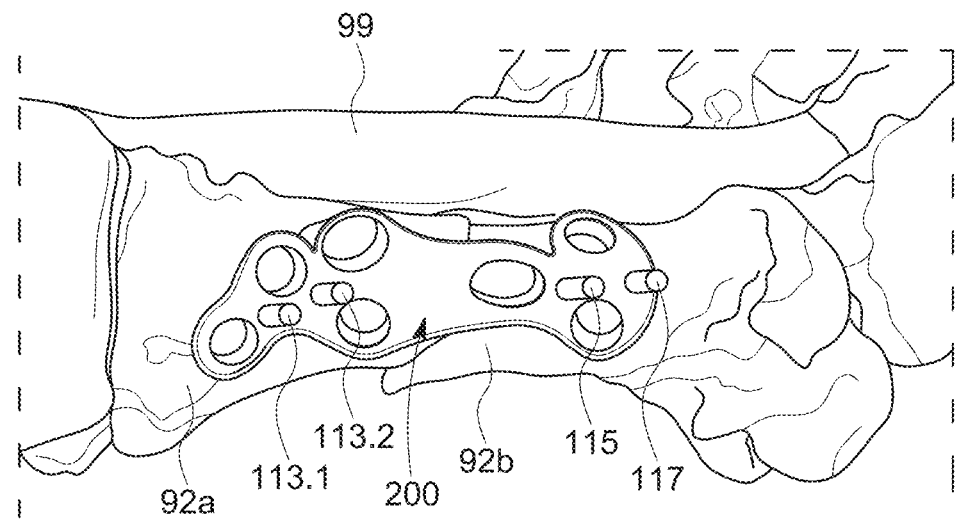
FIG. 5A is a view of an implant for coupling metatarsal bones together.
Figure 5B:
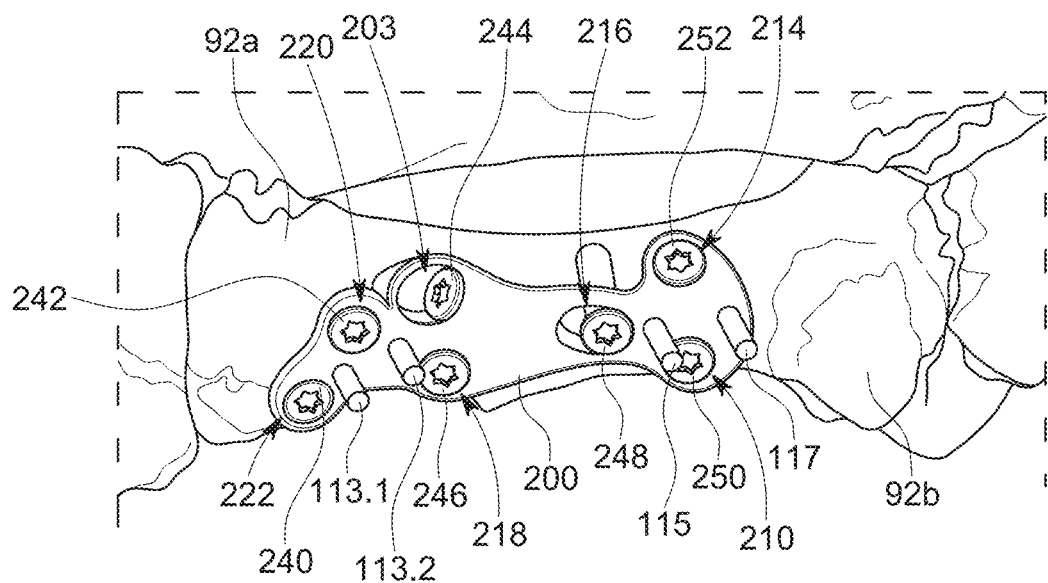
FIG. 5B is another view of the implant.

Next, as shown in FIG. 5A there is a plate 200 which can be inserted over wires 113.1, 113.2, 115 and 117. There is also shown two different sections of metatarsal bone 92a and 92b which can be fused together with plate 200. There is also shown an additional bone 99 disposed adjacent to metatarsal bone 92a and 92b. Plate 200 is shown at least preliminarily coupled to these bones. Next, screws 240, 242, 244, 246, 248, 250, 252 are drilled through drill holes 222, 220, 203, 218, 216, 214, and 210.

Figure 6A:
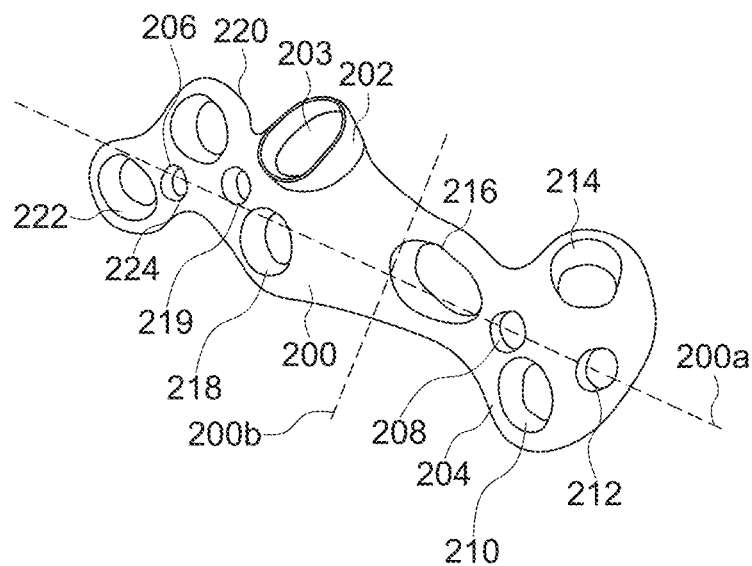
FIG. 6A is a view of the second implant.
Figure 6B:
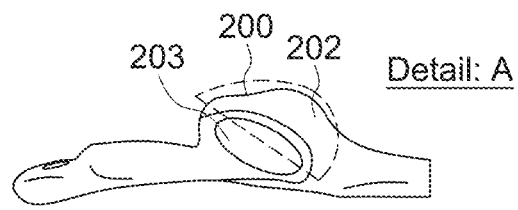
FIG. 6B is a side view of the implant based upon detail A shown in FIG. 6C.
Figure 6C:
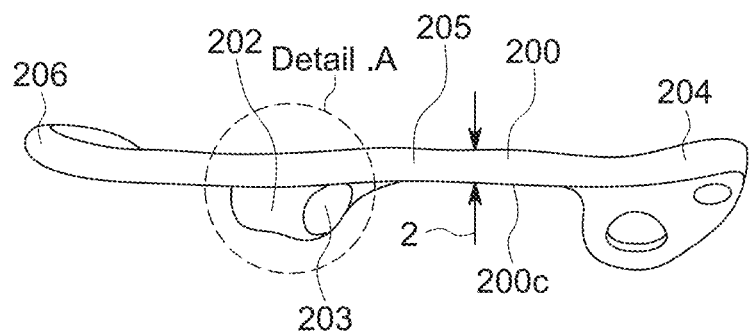
FIG. 6C is a side view of the implant.

As shown in FIG. 6A holes 208, 212, 219, and 224 are used to receive and align the plate via wires 113.1, 113.2, 115 and 117 which were put in place via the previous drill guides. This view of implant 200 shows a longitudinal axis 200a and a latitudinal axis 200b. Screw holes 222, 220, 218, 203, 216, 210, and 214 are shown, which may be threaded. Screw hole 216 is shown as being oblong to allow for some adjustment laterally, such as along or substantially along longitudinal axis 200a. Screw hole 203, is shown in greater detail in FIG. 6B as well as in FIG. 6C. In these views this screw hole 203 is shown extending out from a surface or face of implant 200. As shown in FIGS. 6A and 6C, there are ends of the implant 204 and 206 which are at either ends along longitudinal axis 200a. The shape of implant 200 is such that it is elongated with two ends 206 and 204, with two screw holes 220 and 222 at first end 206, and two screw holes 210 and 214 at a second end 204. Three screw holes 203, 218 and 216 are positioned in a substantially central region. Screw holes 220, 222, 218, 210 and 214 are substantially symmetrically round screw holes with a beveled edge and which open substantially transverse to a surface or a plane of an adjacent section of the implant 200. Screw hole 216 is substantially elongated, with a beveled edge. Screw hole 203 is substantially raised and angled away from an adjacent surface of implant 200. The angle of orientation of screw hole 203 allows for an angled screw to be inserted which extends at an angle substantially offset from a position of perpendicular to an adjacent surface 200c (See FIGS. 6C and 6D) of the implant 200.

Figure 6D:
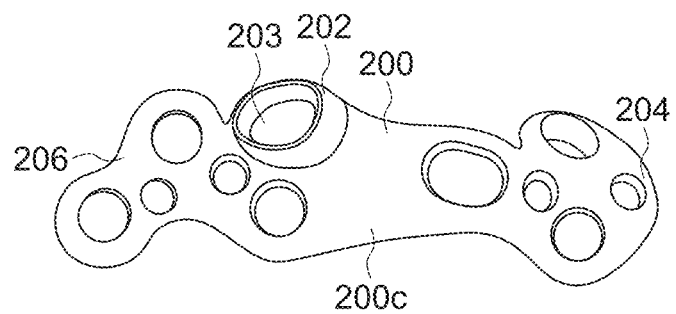
FIG. 6D is a top view of the implant.
Figure 6E:
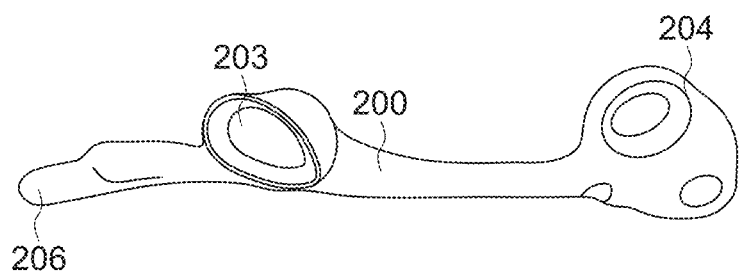
FIG. 6E is a side view of the implant.
Figure 6F:
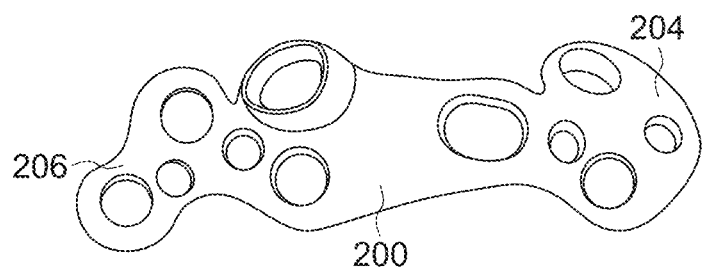
FIG. 6F is a top view of the second implant.

FIG. 6D shows a top or plan view of implant 200 which shows end 206, and opposite end 204, as well as screw hole 203 formed in a raised ridge 202. FIG. 6E also shows ends 206 and 204 as well as hole 203 in implant 200. FIG. 6F shows another plant view of the implant 200 which has ends 206 and 204.

Figure 7A:
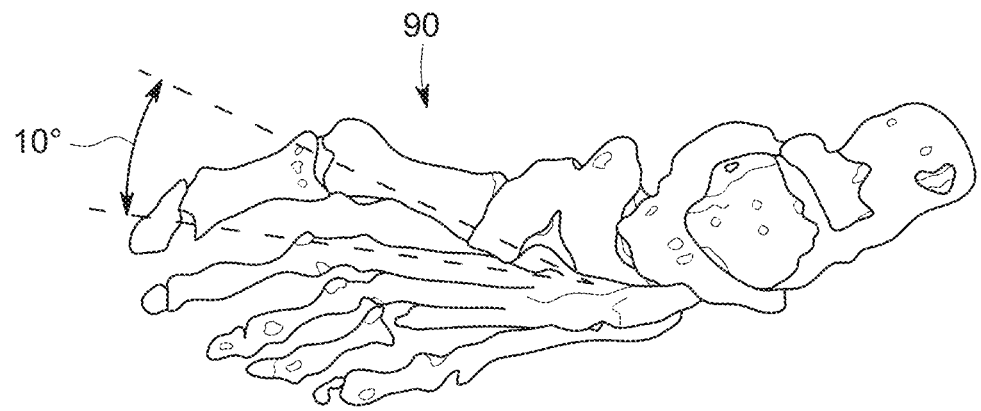
FIG. 7A is a top view of a foot.
Figure 7B:
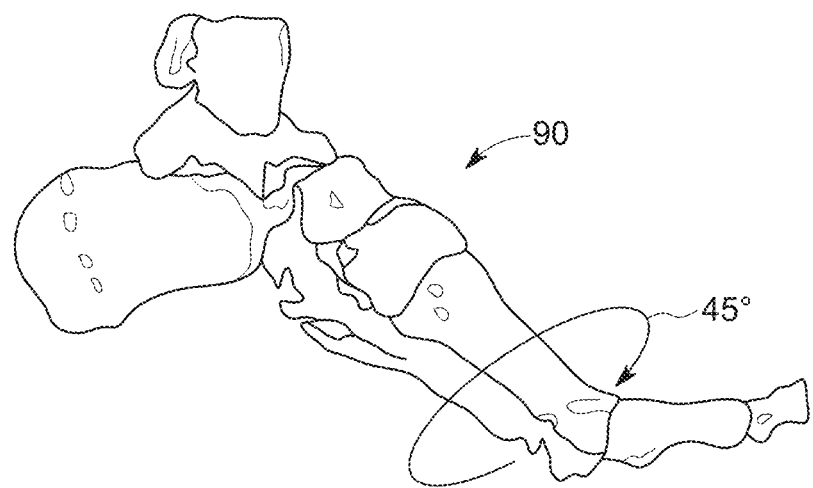
FIG. 7B is a side view of a foot.
Figure 7C:
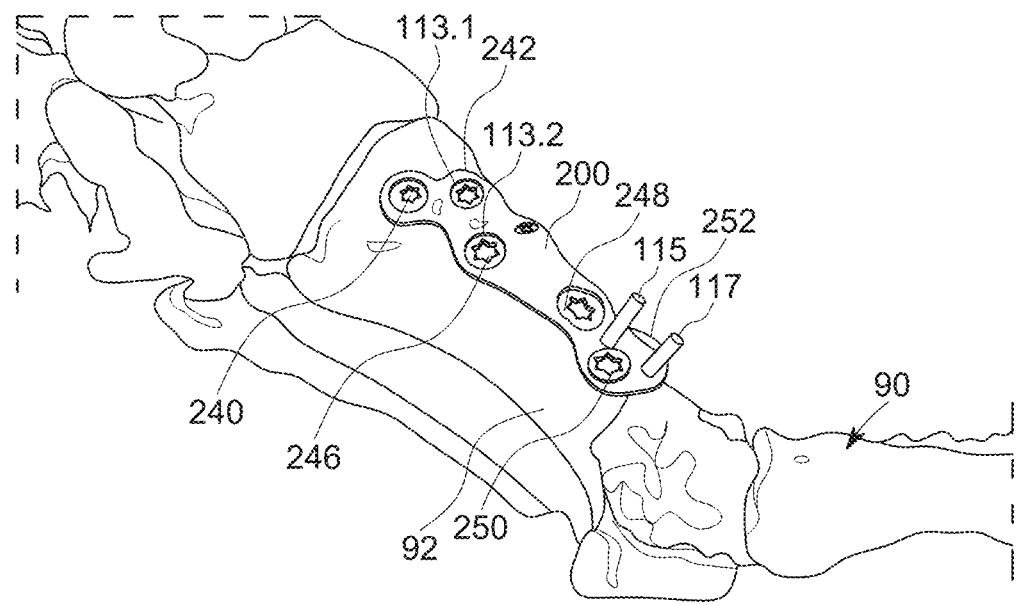
FIG. 7C is a side view of a foot with the implant.
Figure 7D:
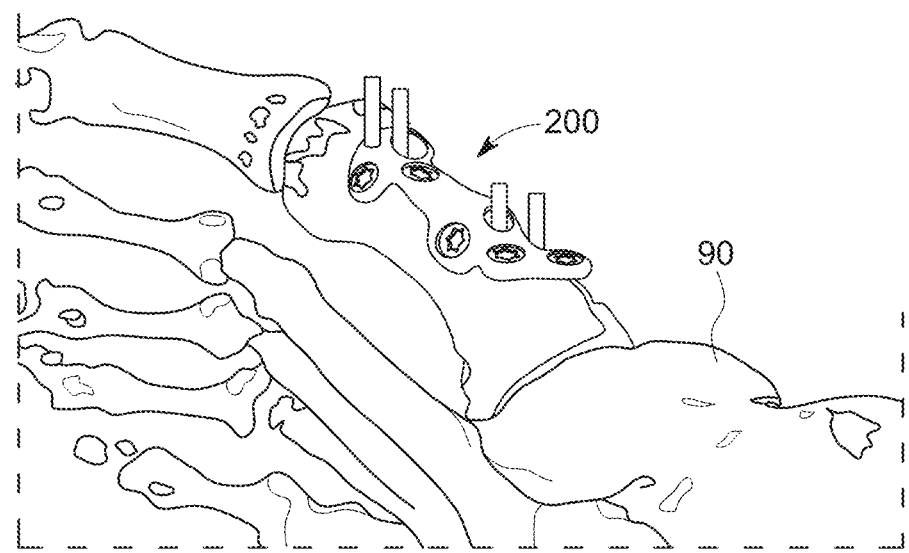
FIG. 7D is a top view of the implant positioned on a foot.

FIG. 7A shows a foot 90 having an angle of offset for a toe being approximately 10 degrees. In addition, FIG. 7B shows an angle of rotation in the foot of 45 degrees. FIG. 7C shows the implant 200 being coupled to a metatarsal bone of a foot such as foot 90. There is shown screws 240, 242, 246, 248, 250 and 252 screwed into plate 200 and into metatarsal bone 92. These screws thereby secure plate 200 to metatarsal bone 92 allowing it to fuse together to fix an ailment in a person such as a bunion.

Accordingly, while at least one embodiment of the present invention have been shown and described, it is to be understood that many changes and modifications may be made thereunto without departing from the spirit and scope of the invention as defined in the appended claims.

What is claimed is:

1. A kit for setting an implant on bone segments, comprising:
a first drill guide comprising a plurality of parts that comprises a first plate part and a second plate part that is separate and distinct from the first plate part, said first drill guide having a first plurality of wire holes comprising a plurality of raised wire holes;
a second drill guide comprising at least one wire hole and at least one screw hole; and
an implant configured to fuse the bone segments together, comprising at least one plate having a plurality of holes, a substantially longitudinal extension, a first end section, a second end section, and a middle section,
wherein the plurality of holes of the implant comprise:
a second plurality of wire holes; and
a first plurality of screw holes,
wherein said second plurality of wire holes are configured to receive wires that place the implant on the bone segments and thereby align the implant and the bone segments in a particular rotated arrangement of the bone segments,
wherein said first plurality of screw holes are configured to receive screws to secure the implant to the bone segments and thereby secure the particular rotated arrangement of the bone segments, and
wherein a plurality of screw holes of said first plurality of screw holes of the implant are beveled,
wherein the first plate part of the first drill guide comprises a front face surface and a first plurality of raised wire holes of the plurality of raised wire holes that extend out transverse past the front face surface of the first plate part, and the second plate part of the first drill guide comprises a front face surface, a second plurality of raised wire holes of the plurality of raised wire holes that extend out transverse past the front face surface of the second plate part, and a raised ridge with a plurality of provisional osteotomy holes that extends out transverse past the front face surface of the second plate part, and wherein the first plurality of raised wire holes are oriented at different orientations than the second plurality of raised wire holes such that the first plurality of raised wire holes are non-parallel to the second plurality of raised wire holes when the first plate part and the second plate part are coupled together longitudinally next to each other and with their front face surfaces substantially aligned with each other.

2. The kit as in claim 1, wherein said first end section has a first plurality of holes of said plurality of holes, said second end section has a second plurality of holes of said plurality of holes, and said middle section has a third plurality of holes of said plurality of holes.

3. The kit as in claim 1, wherein the first drill guide has a longitudinal axis extending substantially along a length of the first drill guide, and a latitudinal axis extending substantially along a width of the first drill guide, and wherein the plurality of provisional osteotomy holes are arranged substantially along the latitudinal axis of the first drill guide.

4. The kit as in claim 3, wherein the second plate part has wings configured to receive said at least one insert of the first plate part of the first drill guide to couple the first and second plate parts of the first drill guide together longitudinally next to each other and with their front face surfaces substantially aligned with each other.

5. The kit as in claim 1, wherein at least one screw hole of the first plurality of screw holes of the implant is raised above a top surface on the implant.

6. The kit as in claim 1, wherein a plurality of screw holes of said first plurality of screw holes of the implant are threaded.

7. The kit as in claim 1, wherein the first plate part has at least one insert.

8. The kit as in claim 1, wherein the first drill guide has a longitudinal axis extending substantially along a length of the first drill guide, and a latitudinal axis extending substantially along a width of the first drill guide, and wherein the plurality of provisional osteotomy holes are arranged and aligned substantially along the latitudinal axis of the first drill guide.

9. A process for correcting a bunion condition, comprising:
applying a first multi-part drill guide to a metatarsal bone, the first drill guide comprising a first drill guide portion with a first plurality of wire holes, and a second drill guide portion with a second plurality of wire holes, wherein the first and second drill guide portions are separate and distinct parts;
inserting a plurality of wires into said metatarsal bone, comprising inserting a first plurality of wires into a first portion of the metatarsal bone via said first plurality of wire holes of the first drill guide portion of said first drill guide, and a second plurality of wires into a second portion of the metatarsal bone via said second plurality of wire holes of the second drill guide portion of said first drill guide;
removing said first drill guide portion from the first portion of said metatarsal bone but leaving said first plurality of wires inserted in said first portion of said metatarsal bone;
removing said second drill guide portion from the second portion of said metatarsal bone but leaving said second plurality of wires inserted in said second portion of said metatarsal bone;
applying a second drill guide to the metatarsal bone by coupling said second drill guide to said second portion of said metatarsal bone by sliding said second drill guide on said second plurality of wires inserted in said second portion of said metatarsal bone via a third plurality of wire holes of the second drill guide;
adjusting a relative rotational position between the first and second portions of said metatarsal bone; and
after the relative rotational position of the first and second portions of said metatarsal bone is adjusted, applying an implant on the first and second portions of the metatarsal bone by inserting the implant over said first plurality of wires and said second plurality of wires, and then coupling said implant to the first and second portions of the metatarsal bone via driving a plurality of screws through a first plurality of screw holes of the implant and into the first portion of the metatarsal bone and driving a plurality of screws through a second plurality of screw holes of the implant and into the second portion of the metatarsal bone,
wherein the first drill guide portion comprises a raised ridge that comprises a plurality of provisional osteotomy holes that are substantially aligned with each other.

10. The process as in claim 9, further comprising:
taking a scan of the metatarsal bone prior to said applying the first multi-part drill guide to said metatarsal bone.

11. The process as in claim 9, wherein said second drill guide comprises a raised screw hole.

12. The process as in claim 11, wherein at least one of the first plurality of screw holes and the second plurality of screw holes of said implant comprises at least one raised screw hole that extends substantially offset or transverse to an extension of at least one of said first plurality of wires or said second plurality of wires, respectively, when the implant is applied on the first and second portions of the metatarsal bone.

13. The process as in claim 9, wherein the first drill guide portion is elongated along a longitudinal direction, wherein the first drill guide portion comprises a longitudinal axis extending substantially along a longitudinal length of the first drill guide portion in the longitudinal direction, and a latitudinal axis extending substantially along a lateral width of the first drill guide portion in a lateral direction, and wherein the raised ridge and the plurality of provisional osteotomy holes are arranged substantially along the latitudinal axis of the first drill guide portion.

14. The process as in claim 9, wherein at least one screw hole of the first plurality of screw holes or at least one screw hole of the second plurality of screw holes of the implant are beveled.

* * * * *